United States Patent [19]

Hood

[11] Patent Number: 5,643,886
[45] Date of Patent: Jul. 1, 1997

[54] AVERMECTINS AND MILBEMYCINS TO TREAT PARASITIC INFESTATIONS IN DOGS

[75] Inventor: John Dick Hood, Betchworth, England

[73] Assignee: Pfizer Inc., New York, N.Y.

[21] Appl. No.: 64,080

[22] PCT Filed: Nov. 11, 1991

[86] PCT No.: PCT/GB91/01981

§ 371 Date: Jan. 7, 1994

§ 102(e) Date: Jan. 7, 1994

[87] PCT Pub. No.: WO92/08455

PCT Pub. Date: May 29, 1992

[30] Foreign Application Priority Data

Nov. 16, 1990 [GB] United Kingdom ............... 9024927

[51] Int. Cl.$^6$ .................................. A61K 31/70
[52] U.S. Cl. .................................. 514/30
[58] Field of Search .................................. 514/30

[56] References Cited

FOREIGN PATENT DOCUMENTS

| | | |
|---|---|---|
| 0237339 | 9/1987 | European Pat. Off. . |
| 0259779 | 3/1988 | European Pat. Off. . |
| 0260536 | 3/1988 | European Pat. Off. . |
| 0260537 | 3/1988 | European Pat. Off. . |
| 0421568 | 4/1991 | European Pat. Off. . |

OTHER PUBLICATIONS

CA 114:(23) 228634t. 1991.

*Primary Examiner*—Kevin E. Weddington
*Attorney, Agent, or Firm*—Peter C. Richardson; Paul H. Ginsburg; Alan L. Kollar

[57] ABSTRACT

Avermectins and milbemycins to treat endo- and ectoparasitic infestations in dogs.

8 Claims, No Drawings

AVERMECTINS AND MILBEMYCINS TO TREAT PARASITIC INFESTATIONS IN DOGS

This application is a 371 of PCT/GB91/01981 filed Nov. 11, 1991.

This invention relates to a method of treating parasites in dogs.

This invention is particularly concerned with the use of certain avermectins and milbemycins described in EP-A-0 421 568 (U.S. Ser. No. 525,094) for the treatment or prophylaxis of endo- and ectoparasitic infestations of dogs.

The compounds used in this invention have parasiticidal properties, for example against nematodes, and are useful for the treatment of helminthiasis.

The term helminthiasis encompasses diseases of animals caused by infestation with parasitic worms such as Strongyles, Ascarids, hookworms, lungworms, filarial worms and whipworms.

The compounds used in this invention are also active against Arthropods. The phylum Arthropoda comprises insects—such as biting flies, lice, bugs, beetles and fleas—and arachnids—such as mites and ticks.

Thus the present invention provides the use of a compound of general formula (I) as defined below for the manufacture of a medicament for the treatment or prophylaxis of endo and ectoparasitic infestations, especially helminthiasis and arthropod or nematode infestations, in dogs.

The present invention also provides a method of treatment or prophylaxis of endo- and ectoparasitic infestations, especially helminthiasis and anthropod or nematode infestations, which comprises administering an effective non-toxic amount of a compound of general formula (I) as defined below to a dog in need thereof.

This invention is particularly concerned with the use of a compound of general formula (I) to combat round worms, hook worms, whipworms and demodectic mange in dogs. As indicated above, the invention also includes prophylatic treatment against parasites, especially against heartworm, by killing the larval stage.

For use according to the invention the compounds of general formula (I) may be formulated for administration with carriers and adjuvants in any convenient way for use in veterinary medicine, by analogy with known anthelmintics.

In suitable formulations the compounds of general formula (I) may be administered to animals orally (as a paste, drench, bolus, capsule or tablet), parenterally, percutaneously, as a food additive (eg granules, pellets or powder), topically (as a cream, wash or spray), or transdermally (as a pour-on).

The compounds of general formula (I) may be formulated as a mixture with each other and/or with other anthelmintics, insecticides, acaricides or other pharmacologically active substances.

Suitably the composition consists of sufficient material to provide a dose of from 0,001 to 100mg of active ingredient per kg of animal body weight per dose, more suitably 0.01 to 10mg/kg per dose.

A composition for use in the invention may suitably contain from 0.1% by weight, preferably from 1.0 to 60% by weight, of the compound of general formula (I) (based on the total weight of the composition), depending on the method of administration.

It will be appreciated that, in some cases, it will be advisable to repeat the dosing of the infected or potentially infected animal with the compound of general formula (I) according to conventional dosage regimes used with anthelmintics:

The compound used in this invention is an avermectin or milbemycin selected from avermectins and milbemycins having the general formula (I):

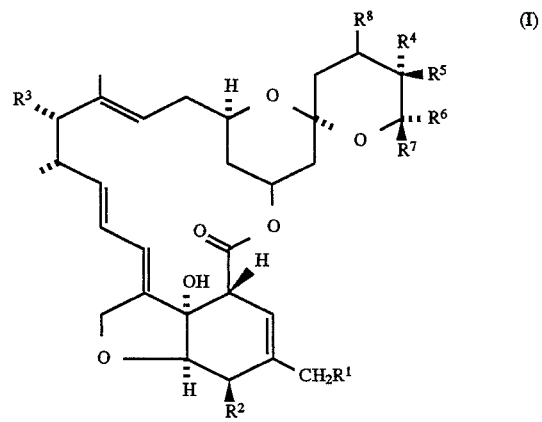

wherein $R^1$ is hydrogen or optionally protected hydroxy; $R^2$ is alkoxy, optionally protected hydroxy, oxo or optionally 0-substituted oximino; $R^3$ is hydrogen, optionally protected hydroxy, or a group 4'-($\alpha$-L-oleandrosyl)-$\alpha$-L-oleandrosyloxy or $\alpha$-L- oleandrosyloxy wherein the terminal hydroxy group is optionally protected; $R^4$, $R^5$, $R^6$ and $R^7$ are the same or different and each is hydrogen or an organic radical; and $R^8$ is an optionally substituted amine or imino group such as optionally 0-substituted oxyimino, optionally N-substituted hydrazone, or optionally N-substituted semicarbazone; with the proviso that the compound of formula (I) is not a compound of formula (E) or (F) below or a compound disclosed in EP-A-0 307 220. Typically $R^3$ is in the $\alpha$-configuration. When $R^3$ is in the $\beta$-configuration then it is preferably optionally protected hydroxy, and/or $R^1$ is preferably hydrogen, and/or $R^2$ is preferably methoxy or optionally protected hydroxy.

EP-A-0 259 779, EP-A-0 293 549, EP-A-0 307 225 and GB-A-2192630 describe compounds of formula (E):

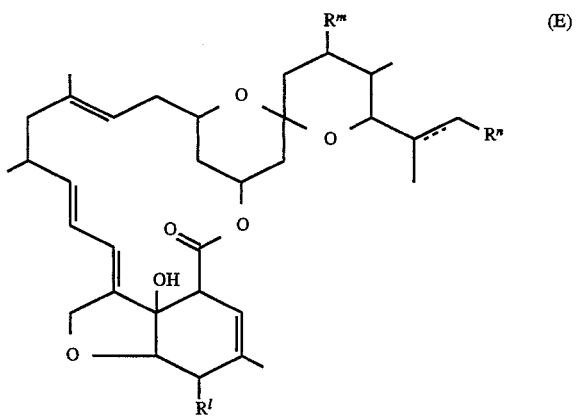

wherein $R^1$ is optionally protected hydroxy or methoxy, $R^m$ is optionally protected hydroxy, oxo, or an imino group such as optionally 0-substituted oxyimino, optionally N-substituted hydrazone, or optionally N-substituted semicarbazone, $R^n$ is methyl, ethyl or isopropyl, and the dashed line is a double bond or an epoxide group.

EP-A-0 260 536 and EP-A-0 260 537 describe compounds of formula (F):

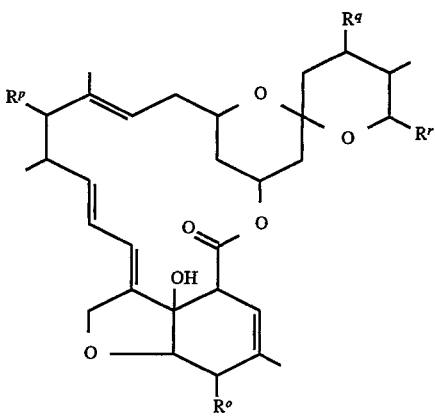

(F)

wherein $R^o$ is optionally protected hydroxy or methoxy, $R^p$ is hydrogen or a sugar residue, $R^q$ is optionally protected hydroxy, oxo, or an imino group such as optionally O-substituted oxyimino or optionally N-substituted hydrazone, and $R^r$ is isopropyl or sec-butyl.

The above compounds of general formula (I) form the subject of EP-A-0 421 568 (U.S. patent application Ser. No. 525,094 filed May 17, 1990, now abandoned) which also describes methods of their preparation and indicates preferred substitutents.

A corresponding disclosure exists in the following numbered patent applications of the countries indicated:

Australia 55140/90; Canada 2017030; Eire 1785/90; Japan 125638/90; Mexico 21897; New Zealand 233680; Portugal 94075; South Africa 90/3703; South Korea 7054/90; Taiwan (ROC) 79104620.

The disclosure of the above-mentioned patent applications is incorporated herein by reference.

Preferably the compound used in the present invention is VS 54396 or VS 55759 disclosed respectively in Example 6 (Z- and E-isomers) and in Example 36 (E-isomer) of EP-A-0 421 568 (U.S. patent application Ser. No. 525,094 filed May 17, 1990; now abandoned). The preparation of these compounds is illustrated below as Examples 1 and 2.

REFERENCE EXAMPLE

23 Oxo-25 (S)-t-butyl milbemycin x

To a solution of (4S)-5,5-dimethyl-4-triethylsilyloxy-1-hexyne (8.3 g, 33 mmol) in THF (100 ml) at −78° C. under a nitrogen atmosphere was added butyllithium (1.6M in hexane, 18.9 ml, 30 mmol) dropwise over a period of 5 mins. and the mixture stirred at −78° C. for a further 3 H. A solution of VS 48927 prepared as described in Examples 1 to 3 of EP-A-0319142 (4.8 g, 8.6 mmol) in THF (20 ml) was added to the mixture which was stirred at −78° C. for a further 15 mins. The reaction was quenched with a cold solution (−−20° C.) of glacial acetic acid (10 ml) in THF (10 ml) and the mixture was then allowed to warm to 0° C. Brine (100 ml) was added and the mixture was extracted with ether (3×100 ml). The combined organic extracts were washed with water, dried (MgSO$_4$) and evaporated to an approximate volume of 50 ml. Methanol (50 ml) was added and the solution again evaporated to an approximate volume of 50 ml. 4-Toluenesulphonic acid (1 g) was added and the mixture stirred at 20° C. for 1 h.

Sodium bicarbonate (100 ml) was added to the mixture and the whole extracted with dichloromethane (3×100 ml). The combined organic extracts were washed with brine (100 ml), dried (MgSO$_4$) and evaporated. The residue was purified by column chromatography (silica eluted initially with dichloromethane and subsequently gradient eluted with 10–60% ethyl acetate in hexane) to afford the methylacetal (3.35 g, 66%).

This product (3.35 g 5.7 mmol) was dissolved in methanol (25 ml) and a solution of mercuric oxide (56 mg, 0.26 mmol) water (3.5 ml) and concentrated sulphuric acid (0.75 ml, 14 mmol)was added dropwise at 20° C. The mixture was stirred at 20° C. for 2 h., water was added and the mixture was extracted with dichloromethane (3×100 ml). The combined organic layers were washed with sodium bicarbonate solution (100 ml), dried (MgSO$_4$) and evaporated to give the title ketone (3.2 g)) pure by nmr + tlc.

EXAMPLE 1

VS 54396 (=Z-isomer)

23-Oxo-25(S)-t-butyl milbemycin X (50 mg, 0.09 mmol) was dissolved in methanol (5 ml). A solution of methoxylamine hydrochloride (50 mg, 0.60 mmol) in water (2 ml) was added and the mixture stirred at room temperature (1h). The reaction mixture was concentrated and then treated with water (30 ml) and extracted with ether (3×15 ml). The combined ethereal extracts were dried (MgSO$_4$) and evaporated. The 1:1 mixture* of Z and E oximes was separated by silica gel preparative thin layer chromatography with hexane - ethyl acetate, 1:1 as eluant.

The 23(Z)-methoxyimino-25(S)-t-butyl milbemycin X was obtained as a white solid (yield 16 mg) $^{M/}Z$ (FAB $^{Na+/Noba}$) 622 [MNa]$^+$50% (relative intensity). Hplc retention time =7.7 min.

The 23(E)-methoxyimino-25(S)-t-butyl milbemycin X was obtained as a white solid (yield 16 mg) $^{M/}Z$ (FAB $^{Na+/Noba}$) 622 [MNa]$^+$25% (relative intensity). Hplc retention time =7.9 min.

Hplc conditions: Dynamax C18 column (25 cm×4.6 mm id) eluted with methanol—water , 9: 1 at 1 ml/min monitored at 245 nm. * Ratio is dependent upon the pH of the reaction mixture.

EXAMPLE 2

VS 55759 (=E-isomer)

To a solution of 23-oxo-25(S)-t-butyl milbemycin X (60 mg 0.1 mmol) and sodium acetate (300 mg, 2.2 mmol) in methanol (3 ml) was added 0-t-butylhydroxylamine hydrochloride (50 mg, 0.4 mmol). The mixture was stirred at 20° C. for 1 h., water (10 ml) was added and the whole mixture extracted with dichloromethane (3×15 ml). The combined organic extracts were washed with water, dried (MgSO$_4$) and evaporated to dryness. Purification by preparative t.l.c., (silica taper plate (Analtech$^R$) eluted with ethyl acetate/ hexane 2:5) yielded a 4:1 mixture of E:Z oxime isomers (54 mg). Treatment of a portion of this mixture (30 mg) with methanol (2 ml) and hydrochloric acid (1M, 0.2 ml) gave a 1:1 E:Z ratio of oxime isomers. The two isomers were separated by preparative t.l.c. (silica taperplate eluted four times with chloroform).

23(Z)-t-butyloxyimino-25(S)-t-butyl milbemycin X:

tlc $R_f$=0.5 (Silica eluted three times with chloroform containing 1.5% ethanol) m/z (FAB Na$^+$/Noba) (relative intensity) 664 [MNa]$^+$(95%)

23(E)-t-butyloxyimino-25(S)-t-butyl milbemycin X: tlc $R_f$=0.45 (Silica eluted three times with chloroform containing 1.5% ethanol) m/z (FAB Na$^+$/Noba) (relative intensity) 664 [MNa]$^+$(95%).

Hplc retention times: Dynamax 60A Silica column (25 cm×4.6 mm id) eluted with chloroform/methanol 99:1 at 1 ml/min monitored at 245 nm.

Retention time 23-Z isomer=14.2 min.

Retention time 23-E isomer=15.4 min.

Efficacy of VS-54936 and VS-55759 against Dirofilaria immitis in dogs

Method

Twenty-one adult male and 21 adult female beagle dogs were used. The dogs weighed between 7.8 and 11.3 kg, and their ages ranged from 12 to 13 months. Blood from all of the 42 dogs was collected prior to initiation of the study and at 4.5 months postinfection and examined by the modified Knott's method to ascertain that the dogs were not infected with either D. immitis or Dipetalonema reconditum.

On day 0 each dog was given 50 infective larvae of p. immitis as described by McCall (J. Georgia Entomol. Soc. 16(2), 1981). The dogs were weighed on Day 23 and allocated to treatment groups. Six replicates of 7 dogs each were formed by ranking dogs by weight within the sex. Within each replicate, the dogs were randomly allocated to 1 of 7 treatment groups using a table of random numbers (Bhattacharyya, G.K. and R.A. Johnson, Statistical Concepts and Methods, John Wiley and Sons, N.Y., 1977, Table 14, pp. 623–624), such that 7 groups of 6 dogs each (3 males and 3 females) were formed.

On Day 30 i.e., 30 days post-infection, each dog was dosed orally with a gelatin capsule containing the compound under test.

All dogs were killed on the same day at 149 days after inoculation of infective larvae of D. immitis.

The pleural and peritoneal cavities were examined for immature and mature adult worms of D. immitis, and the anterior and posterior venae cavae and the azygous vein were ligated before removal of the heart and lungs. The precava, right atrium, right ventricle, and pulmonary arteries (including those coursing through the lungs) were dissected and examined for worms. The worms from each dog were recorded as either dead or alive and either immature or mature.

Results

The groups treated at 0.01 mg/kg with VS 54936 or VS 55759, all dogs were free of worms. No adverse reactions associated with treatment were observed for any treated animal in any of the treatment groups.

Efficacy of VS-55759 and VS-54936 for control of Demodex canis Infesting Dogs

Method

Fifteen dogs of beagle breeding with natural Demodex infestations were preconditioned. Preconditioning included worming and vaccinations for distemper, hepatitis, leptospirosis, parvovirus and parainfluenza.

The fifteen dogs were subdivided into five groups of three dogs per treatment group. The dogs were housed one per pen and group isolated to avoid cross-contamination. Food and water was available ad libitum.

The compounds under test were administered by subcutaneous injection on three occasions at 0.7 and 14 days.

Efficacy was determined by skin scraping and clinical observations. The skin was scraped and scrapings examined to determine Demodex mite populations. A small amount of mineral oil was applied to an infested area on the belly, legs, feet, or face, and approximately 12 square centimeters of skin was scraped with a scalpel. The skin was scraped until blood was observed. The total amount of material collected was diluted with mineral oil and microscopically examined for mites and eggs. Observations were mapped on each quarter of each dog at each observation period on days 21, 28, 35 and 42.

Results

Dogs treated with 3×200 mg of VS 54396 and VS 55759 were clear of mites at day 35 and day 21 respectively and remained clear until the end of the trial.

No adverse reactions to treatment were noted.

I claim:

1. A pharmaceutical composition for use in treatment or prophylaxis of endo- and ectoparasitic infestations in dogs, which comprises a compound of formula (I):

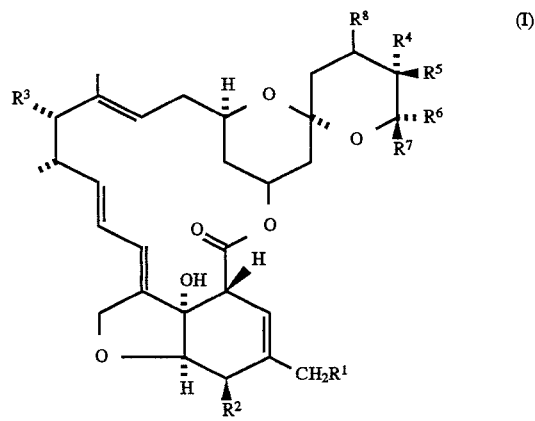

wherein $R^1$ is selected from the group consisting of hydrogen, hydroxy, and protected hydroxy;

$R^2$ is selected from the group consisting of alkoxy, hydroxy, protected hydroxy, oxo, oximino, and O-substituted oximino;

$R^3$ is selected from the group consisting of hydrogen, hydroxy, protected hydroxy, 4'-(α-L-oleandrosyl)-α-L-oleandrosyloxy, 4'-(α-L-oleandrosyl)-α-L-oleandrosyloxy, wherein the terminal hydroxy group is protected, α-L-oleandrosyloxy, and α-L-oleandrosyloxy wherein the terminal hydroxy group is protected;

$R^4$, $R^5$, $R^6$, and $R^7$ are independently selected from the group consisting of hydrogen and an organic radical;

$R^8$ is selected from the group consisting of amino, substituted amino, imino, and substituted imino;

provided that

A) if $R^2$ is hydroxy or protected hydroxy; $R^3$ is hydrogen; $R^4$ is hydrogen or methyl; $R^5$ is hydrogen or methyl; and $R^8$ is imino, oxyimino, O-substituted oxyimino, hydrazone, N-substituted hydrazone, semicarbazone, or N-substituted semicarbazone;

then i) $R^1$ is hydroxy or protected hydroxy; and further provided that (a) when $R^6$ is hydrogen, $R^7$ is not cis-C(CH$_3$)=CHR$^n$, where $R^n$ is selected from the group consisting of methyl, ethyl, and isopropyl; (b) when $R^7$ is hydrogen, $R^6$ is not cis-C(CH$_3$)=CHR$^n$, where $R^n$ is selected from the group consisting of methyl, ethyl, and isopropyl; (c) when $R^6$ is hydrogen, $R^7$ is not

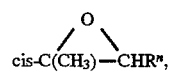

where $R^n$ is selected from the group consisting of methyl, ethyl, and isopropyl; (d) when $R^7$ is hydrogen, $R^6$ is not

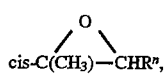

where $R^n$ is selected from the group consisting of methyl, ethyl, and isopropyl;

B) if $R^2$ is hydroxy or protected hydroxy; $R^3$ is hydrogen; $R^4$ is hydrogen or methyl; $R^5$ is hydrogen or methyl; $R^6$ is hydrogen, isopropyl, or sec-butyl; $R^7$ is hydrogen, isopropyl, or sec-butyl; and $R^8$ is imino, oxyimino, O-substituted oxyimino, hydrazone, or N-substituted hydrazone;

then i) $R^1$ is hydroxy or protected hydroxy;

C) if $R^2$ is oxo, hydroxy, substituted hydroxy having up to 25 carbon atoms; $R^3$ is hydroxy; $R^4$ is methyl; $R^5$ is hydrogen; $R^6$ is hydrogen; $R^7$ is cis-C(CH$_3$)=CHR$^o$, where $R^o$ is selected from the group consisting of methyl, ethyl, and isopropyl; and $R^8$ is —C=NOR$^p$, where $R^p$ is selected from the group consisting of hydrogen and a $C_{1-8}$ alkyl group:

then i) $R^1$ is hydroxy or protected hydroxy;

said compound of formula (I) being the E or Z isomer, or a mixture thereof.

2. A composition according to claim 1, in the form of an oral formulation.

3. A composition according to claim 1, in the form of an injectable formulation.

4. A composition according to claim 1, in the form of a pour-on formulation.

5. A method for the treatment or prophylaxis of endo- and ectoparasitic infestations in dogs, which method comprises the administration to a dog in need thereof of an effective amount of a compound of formula (I):

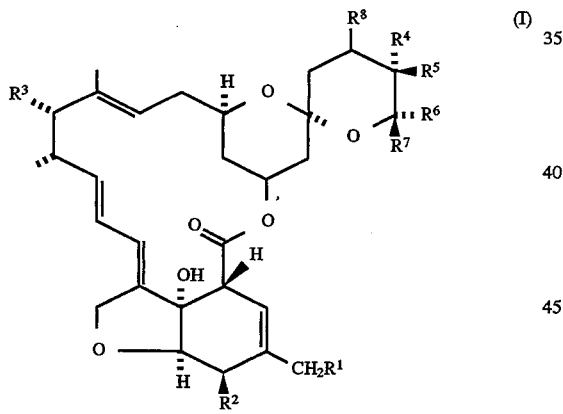

wherein $R^1$ is selected from the group consisting of hydrogen, hydroxy, and protected hydroxy;

$R^2$ is selected from the group consisting of alkoxy, hydroxy, protected hydroxy, oxo, oximino, and O-substituted oximino;

$R^3$ is selected from the group consisting of hydrogen, hydroxy, protected hydroxy, 4'-($\alpha$-L-oleandrosyl)-$\alpha$-L-oleandrosyloxy, 4'-($\alpha$-L-oleandroyl)-$\alpha$-L-oleandrosyloxy wherein the terminal hydroxy group is protected, $\alpha$-L-oleandrosyloxy, and $\alpha$-L-oleandrosyloxy wherein the terminal hydroxy group is protected;

$R^4$, $R^5$, $R^6$, and $R^7$ are independently selected from the group consisting of hydrogen and an organic radical;

$R^8$ is selected from the group consisting of amino, substituted amino, imino, and substituted imino;

provided that

A) if $R^2$ is hydroxy or protected hydroxy; $R^3$ is hydrogen; $R^4$ is hydrogen or methyl; $R^5$ is hydrogen or methyl; and $R^8$ is imino, oxyimino, O-substituted oxyimino, hydrazone, N-substituted hydrazone, semicarbazone, or N-substituted semicarbazone;

then i) $R^1$ is hydroxy or protected hydroxy; and further provided that (a) when $R^6$ is hydrogen, $R^7$ is not cis-C(CH$_3$)=CHR$^n$, where $R^n$ is selected from the group consisting of methyl, ethyl, and isopropyl; (b) when $R^7$ is hydrogen, $R^6$ is not cis-C(CH$_3$)=CHR$^n$, where $R^n$ is selected from the group consisting of methyl, ethyl, and isopropyl; (c) when $R^6$ is hydrogen, $R^7$ is not

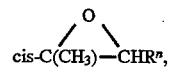

where $R^n$ is selected from the group consisting of methyl, ethyl, and isopropyl; (d) when $R^7$ is hydrogen, $R^6$ is not

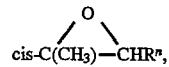

where $R^n$ is selected from the group consisting of methyl, ethyl and isopropyl;

B) if $R^2$ is hydroxy or protected hydroxy; $R^3$ is hydrogen; $R^4$ is hydrogen or methyl; $R^5$ is hydrogen or methyl; $R^6$ is hydrogen, isopropyl, or sec-butyl; $R^7$ is hydrogen, isopropyl, or sec-butyl; and $R^8$ is imino, oxyimino, O-substituted oxyimino, hydrazone, or N-substituted hydrazone;

then i) $R^1$ is hydroxy or protected hydroxy;

C) if $R^2$ is oxo, hydroxy, substituted hydroxy having up to 25 carbon atoms; $R^3$ is hydroxy; $R^4$ is methyl; $R^5$ is hydrogen; $R^6$ is hydrogen; $R^7$ is cis-C(CH$_3$)=CHR$^o$, where $R^o$ is selected from the group consisting of methyl, ethyl, and isopropyl; and $R^8$ is —C=NOR$^p$, where $R^p$ is selected from the group consisting of hydrogen and a $C_{1-8}$ alkyl group;

then i) $R^1$ is hydroxy or protected hydroxy;

said compound of formula (I) being the E or Z isomer, or a mixture thereof.

6. A method according to claim 5, wherein said method is for the treatment of endoparasitic and ectoparasitic infestations selected from the group consisting of roundworm, hookworm, whipworm and/or demodectic mange.

7. A method according to claim 5, wherein said method is for the prophylaxis of heartworm infestation.

8. A method according to claim 5, wherein $R^1$, $R^3$, $R^4$, $R^5$ and $R^6$ are hydrogen, $R^2$ is hydroxy, $R^7$ is t-butyl and $R^8$ is methoxyimino or t-butyloxyimino, the E- or Z-isomer or a mixture thereof.

* * * * *